(12) United States Patent
Sawa et al.

(10) Patent No.: US 10,094,753 B2
(45) Date of Patent: Oct. 9, 2018

(54) HARDNESS TESTER

(71) Applicant: MITUTOYO CORPORATION, Kanagawa (JP)

(72) Inventors: Takeshi Sawa, Kawasaki (JP); Fumihiko Koshimizu, Zama (JP)

(73) Assignee: MITUTOYO CORPORATION, Kanagawa (JP)

( * ) Notice: Subject to any disclaimer, the term of this patent is extended or adjusted under 35 U.S.C. 154(b) by 260 days.

(21) Appl. No.: 15/251,295

(22) Filed: Aug. 30, 2016

(65) Prior Publication Data

US 2017/0074763 A1    Mar. 16, 2017

(30) Foreign Application Priority Data

Sep. 10, 2015  (JP) .................. 2015-178032

(51) Int. Cl.
    *G01N 3/42*    (2006.01)
(52) U.S. Cl.
    CPC ....... *G01N 3/42* (2013.01); *G01N 2203/0206* (2013.01)
(58) Field of Classification Search
    CPC .................. G01N 2203/0206; G01N 3/42
    See application file for complete search history.

(56) References Cited

U.S. PATENT DOCUMENTS

| | | | |
|---|---|---|---|
| 2009/0107221 A1* | 4/2009 | Ernst .................. | G01N 3/42 73/81 |
| 2013/0047712 A1* | 2/2013 | Ariga .................. | G01N 3/42 73/81 |
| 2013/0047713 A1* | 2/2013 | Ariga .................. | G01N 3/068 73/81 |
| 2013/0068001 A1* | 3/2013 | Sadahiro ............. | G01N 3/42 73/81 |
| 2014/0294282 A1* | 10/2014 | Miyakura ............ | G06T 7/001 382/141 |

FOREIGN PATENT DOCUMENTS

JP         4750314 B     8/2011

* cited by examiner

*Primary Examiner* — Francis C Gray
(74) *Attorney, Agent, or Firm* — Greenblum & Bernstein, P.L.C.

(57) ABSTRACT

A hardness tester forms an indentation on a surface of a sample by loading a predetermined test force with an indenter and measures a hardness of the sample using the indentation. The hardness tester includes a light source emitting light on the surface of the sample and forming an illumination pattern having a spot; and a controller forming the indentation by bringing the indenter into contact with the sample in a state where a perpendicular line of a vertex of the indenter overlaps a test point when the position of the spot of the illumination pattern formed by the light source on the surface of the sample is used as the test point.

12 Claims, 7 Drawing Sheets

HARDNESS TESTER

CROSS-REFERENCE TO RELATED APPLICATIONS

The present application claims priority under 35 U.S.C. § 119 of Japanese Application No. 2015-178032, filed on Sep. 10, 2015, the disclosure of which is expressly incorporated by reference herein in its entirety.

BACKGROUND OF THE INVENTION

1. Field of the Invention

The present invention relates to a hardness tester.

2. Description of Related Art

A hardness tester is known which measures hardness of a sample by pressing an indenter into a surface of the sample to form an indentation and measuring dimensions of the indentation, or by measuring a pressing depth of the indenter when the indentation is formed. In such a hardness tester, before pressing an indenter, confirmation is required as to whether a pressing position (test point of the sample) is positioned directly beneath the indenter. When using a Rockwell harness tester or a Brinell hardness tester for example, a method to confirm visually is known in which the test point is brought closer to the indenter while lifting a vertical stage arranged immediately beneath a pressing mechanism. In addition, when using a Vickers hardness tester, a method is known in which a microscope measuring an indentation length of the tester is used and the test point is aligned to a predetermined position while surveying the entire surface of the sample. However, in the visual confirmation method, a task of bringing the indenter closer to the sample is performed while observing obliquely, rather than from directly above, with respect to a pressing direction. Therefore, the visual confirmation method may cause a positioning drift relative to an expected position and also take time and effort for adjustments. In addition, in the microscope confirmation method, an approximate test position of the sample must first be identified using a low-magnification field lens, and then the test position of the sample needs to be identified by switching to a high-magnification field lens, thus taking time and effort for adjustments. In addition, when using only the high-magnification field lens, it is difficult to identify the test position of the sample due to a narrow field of view.

In contrast, Japanese Patent No. 4750314, for example, proposes a technology to determine with certainty a test point of a sample in one trial. A ring-shaped illumination pattern is formed on a surface of the sample by a plurality of light sources concentrically installed on an indenter column, and the sample is positioned with fine adjustments to allow the test point of the sample to align with a center of the illumination pattern.

However, in the device described in Japanese Patent No. 4750314, the test point of the sample is adjusted so as to align with the center of the illumination pattern by a visual estimation. Therefore the adjusted position may still be offset from the actual test point.

SUMMARY OF THE INVENTION

The present invention provides a hardness tester capable of adjusting a test point easily and performing an actual test without drift in the adjusted test point.

In order to resolve the above-noted issues, one aspect of the invention is a hardness tester which forms an indentation on a surface of a sample by loading a predetermined test force with an indenter and measures a hardness of the sample using the indentation. The hardness tester includes an illuminator and a controller. The illuminator emits light on the surface of the sample and forms an illumination pattern having a spot. The controller forms the indentation by bringing the indenter into contact with the sample in a state where a perpendicular line of a vertex of the indenter overlaps the test point when the position of the spot of the illumination pattern formed by the illuminator on the surface of the sample is used as the test point.

In another aspect of the invention, the hardness tester includes a sample placement portion on which the sample is placed and a displacement portion displacing the sample placement portion in a horizontal direction. The illuminator includes a single light source which is provided in parallel to the indenter and emits light substantially parallel to a vertical direction. The controller displaces the sample placement portion in the horizontal direction using the displacement portion to allow the perpendicular line of the vertex of the indenter to be positioned at the test point on the surface of the sample.

In another aspect of the invention, the displacement portion includes an XY stage capable of reciprocating displacement of the sample placement portion in two directions inside a horizontal plane. The hardness tester includes a memory storing relative position coordinates of the position of the indenter and the position where the spot of the illumination pattern is formed. The controller displaces the sample placement portion using the displacement portion based on the relative position coordinates stored in the memory.

In another aspect of the invention, the hardness tester includes the sample placement portion on which the sample is placed and the displacement portion displacing the indenter in the horizontal direction. The illuminator includes the single light source which is provided in parallel to the indenter and emits light substantially parallel to the vertical direction. The controller displaces the indenter in the horizontal direction using the displacement portion to allow the perpendicular line of the vertex of the indenter to be positioned at the test point on the surface of the sample.

In another aspect of the invention, the illuminator includes two light sources emitting light in mutually approaching directions. The hardness tester is configured to allow the perpendicular line of the vertex of the indenter to be positioned at the spot where the light emitted from the two light sources intersect. The controller controls a height position of the sample to allow the intersection point of the light emitted from the two light sources and the surface of the sample to overlap.

In another aspect of the invention, the light emitted from the two light sources has a band shape.

In another aspect of the invention, the illuminator includes a light source emitting laser light.

According to the present invention, adjustments of the test point can readily be performed and an actual test can be performed without drift in the adjusted test point.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, embodiments of the present invention are described with reference to the drawings.

First Embodiment

Figure 1:
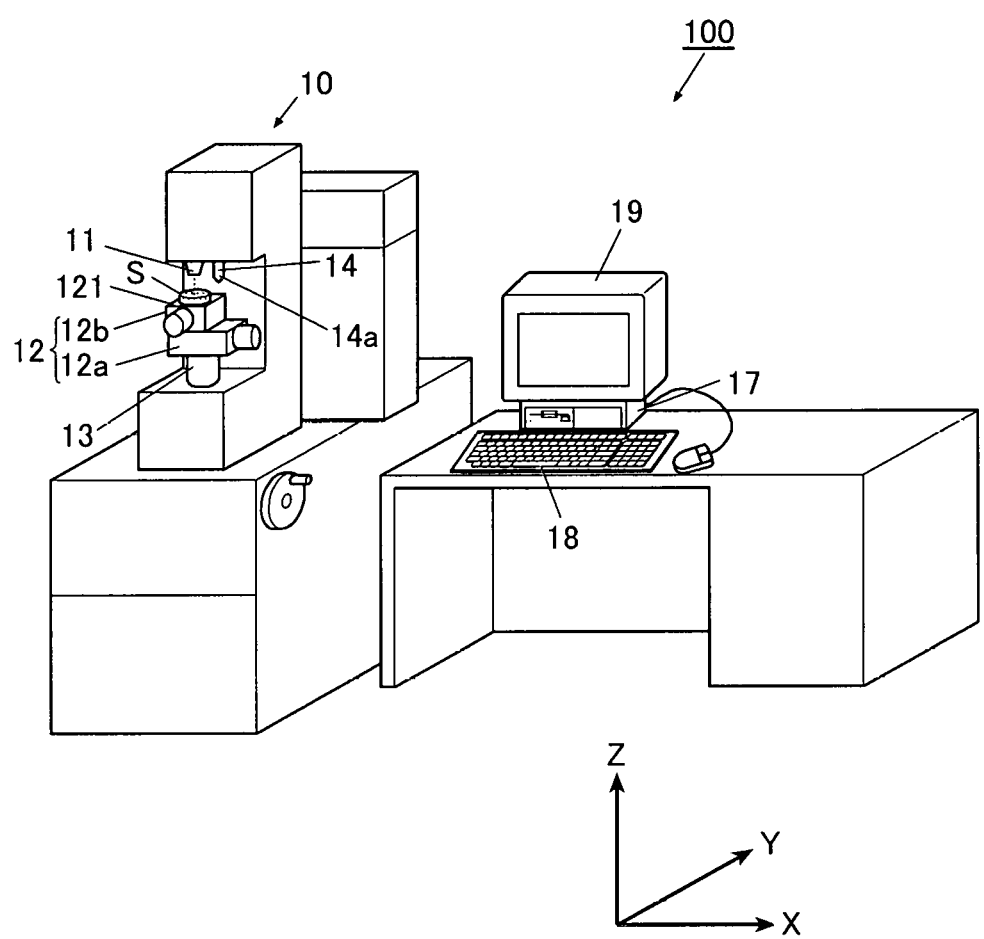
FIG. 1 is an overall diagram of a hardness tester according to the present invention.
Figure 2:
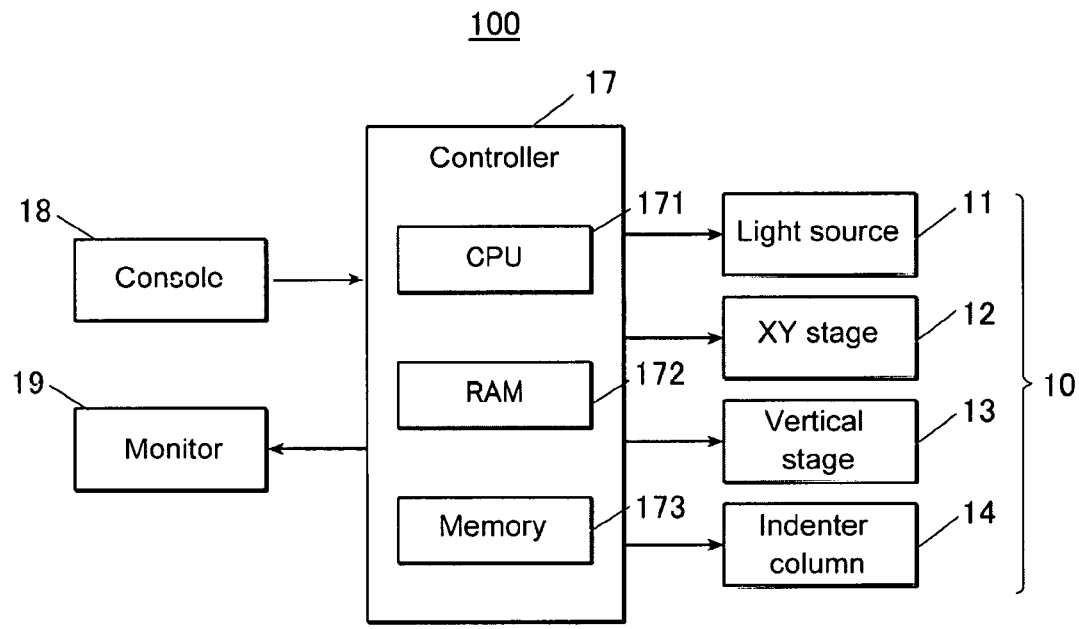
FIG. 2 is a block diagram illustrating a control structure of the hardness tester according to a first embodiment.
Figure 3:
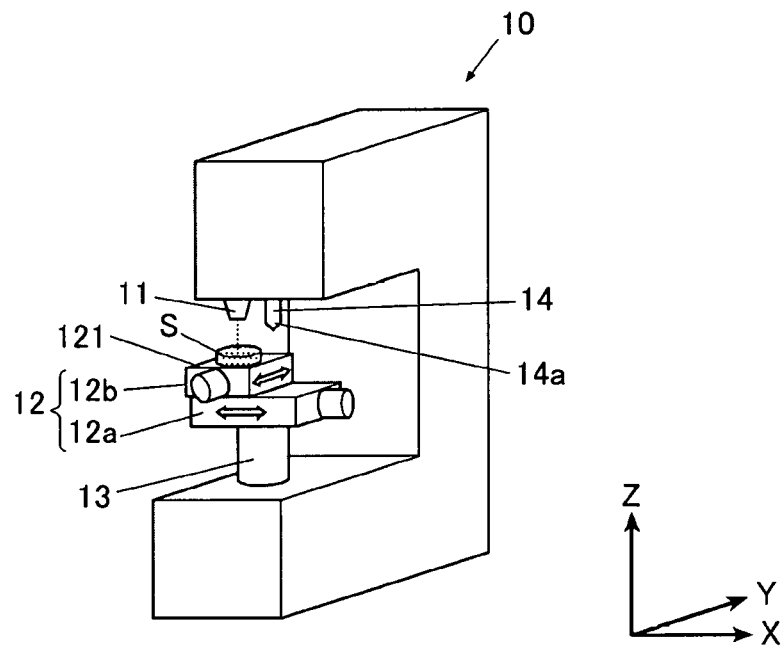
FIG. 3 is a schematic view illustrating a hardness tester main body of the hardness tester of FIG. 2.

Hereafter, a first embodiment of the present invention is described in detail with reference to the drawings. FIG. 1 is an overall diagram of a hardness tester according to the first embodiment. FIG. 2 is a block diagram of a control structure of the hardness tester of FIG. 1. FIG. 3 is a schematic view illustrating a hardness tester main body of the hardness tester of FIG. 2.

As shown in FIGS. 1 to 3, a hardness tester 100 is configured to include a hardness tester main body 10, a controller 17, a console 18, and a monitor 19. The hardness tester 100 is a Rockwell hardness tester, for example. Moreover, in the following description, an X direction is a left-right direction, a Y direction is a front-back direction, and a Z direction is an up-down direction in FIGS. 1 and 3. In addition, an X-Y plane is a horizontal plane.

The hardness tester main body 10, for example, is configured to include a light source (illuminator) 11 emitting light at a sample S, an XY stage 12 (displacement portion or displacer) displacing the sample S in a horizontal direction, a vertical stage 13 lifting and lowering the XY stage 12, and an indenter column 14 having an indenter 14a forming an indentation on the sample S.

The light source 11 includes an LD (Laser Diode), for example, and generates and emits laser light. The light source 11, which is provided in parallel to the indenter column 14, emits light in a Z direction (that is, the direction substantially parallel to the displacement direction of the indenter column 14) and emits the light at the sample S positioned below. A spot-like illumination pattern is displayed at a single point of the sample S placed on the XY stage 12 by the light source 11. In the present embodiment, the position of the spot formed by the light source 11 on the surface of the sample S is the test point. Further, from a viewpoint of creating a low cost device configuration, as described above, the light source generating laser light is used as the light source 11. Alternatively, a light source such as a halogen or an LED (Light Emitting Diode) may be used, for example.

The XY stage 12 is a sample placement portion (sample placement platform) 121 where the sample S can be placed on the top surface and has a known configuration which includes a first stage 12a displaceable in the X direction and a second stage 12b displaceable in the Y direction. The XY stage 12 is driven in response to a control signal output by the controller 17 and slide-displaces the sample S placed atop the XY stage 12 in the X-Y direction. Accordingly, the sample S can be displaced to allow the test point on the surface of the sample S to overlap with a perpendicular line of a vertex of the indenter 14a.

The vertical stage 13 is driven in response to the control signal output by the controller 17 and displaces the XY stage 12 in the Z direction.

The indenter column 14 is displaced toward the sample S with a load mechanism, which is driven in response to the control signal output by the controller 17. The indenter 14a, provided on a forefront end of the indenter column 14, is pressed on the surface of the sample S with a predetermined test force. Accordingly, an indentation is formed on the surface of the sample S. Examples of the indenter 14a being used may include a conical diamond indenter having a tip radius of 0.2 mm and a tip angle of 120 degrees; an indenter using a steel ball of 1/16 inch, 1/8 inch, or the like; and the like.

The controller 17 is configured to include a CPU (Central Processing Unit) 171, a RAM (Random Access Memory) 172, and a memory 173. The controller 17 performs operation control of performance of a predetermined hardness test by executing a predetermined program stored in the memory 173.

Specifically, the CPU 171 retrieves a processing program stored in the memory 173, then opens and executes the processing program in the RAM 172. The CPU 171 thus performs overall control of the hardness tester 100.

The RAM 172 opens the processing program executed by the CPU 171 in a program storage region within the RAM 172 and stores in a data storage region input data, processing results generated during execution of the processing program, and the like.

The memory 173 includes, for example, a recording medium storing a program, data, and the like. The memory 173 stores various kinds of data, various kinds of processing programs, and data processed by running the programs that allow the CPU 171 to perform overall control of the hardness tester 100. For example, relative position coordinates are stored in advance in the memory 173, the relative position coordinates belonging to the position where the spot of the illumination pattern is formed on a top surface of the sample placement portion 121 by the light from the light source 11 and a position lying on the perpendicular line of the vertex of the indenter 14a. The CPU 171 displaces the XY stage 12 based on the coordinates.

The console 18 is configured with a keyboard, a mouse, and the like. The console 18 receives an input operation by a user during the hardness test. When the console 18 receives a predetermined input operation performed by the user, a predetermined operation signal corresponding to the input operation is generated and output to the controller 17. For example, the console 18 receives an operation in which the user inputs a test condition to be used when carrying out the hardness test with the hardness tester 100. A test condition value is a value such as a material of the sample S, a test force (N) loaded on the sample S by the indenter 14a, or position coordinates of the light source 11 and the indenter 14a, for example.

The monitor 19 is configured by a display device such as an LCD (Liquid Crystal Display), for example. The monitor 19 displays the test condition of the hardness test input to the console 18 and results of the hardness test and the like.

Figure 4:
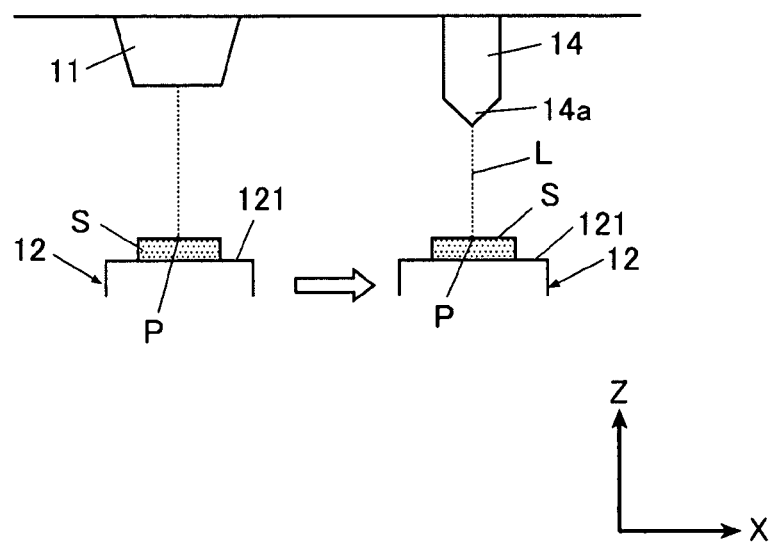
FIG. 4 illustrates a displacement of a sample.

Next, a test point alignment method of the hardness tester 100 according to the present embodiment is described. First, the user places the sample S undergoing the hardness test on the top surface of the XY stage 12 and emits light at the sample S from the light source 11. In addition, the spot-like illumination pattern of the light is used as an index, and fine adjustments are performed to allow the desired test point of the sample S to match the pattern. Accordingly, the position of the spot is a test point P. In this state, when the user gives an instruction to start the test, as shown in FIG. 4, the controller 17 displaces the XY stage 12 based on the position coordinates stored in the memory 173. Accordingly, the test point P of the sample S overlaps the position of a perpendicular line L of the vertex of the indenter 14a. Thereafter, the controller 17 forms the indentation at the test point of the surface of the sample S by operating the indenter 14a and performs predetermined data analysis to calculate the hardness of the sample S.

As described above, according to the present embodiment, the hardness tester 100 forms the indentation on the surface of the sample S by loading the predetermined test force with the indenter 14a and measures the hardness of the sample using the indentation. The hardness tester 100 includes the light source 11 and the controller 17. The light source 11 emits light on the surface of the sample S and forms the illumination pattern having the spot. The controller 17 forms the indentation by bringing the indenter 14a into contact with the sample S in a state where the test point overlaps the perpendicular line of the vertex of the indenter 14a, the test point being the position of the spot of the illumination pattern formed by the light source 11 on the surface of the sample S. Therefore, after the spot-like light is emitted at the desired test point of the sample S and the test point is confirmed, the test can be performed by forming the indentation at the confirmed test point while making simple adjustments and without drifting from the adjusted test point prior to the test.

In addition, according to the present embodiment, the hardness tester 100 includes the sample placement portion 121 on which the sample S is placed and the XY stage 12 on which the sample placement portion 121 is displaced in the horizontal direction. The light source 11, provided in parallel to the indenter 14a, is a single light source emitting light substantially parallel to the vertical direction. The controller 17 displaces the sample placement portion 121 in the horizontal direction using the XY stage 12 to allow the perpendicular line of the vertex of the indenter 14a to be positioned at the test point on the surface of the sample S. Accordingly, due to the configuration in which the light source 11 and the indenter 14a do not overlap, the confirmation of the test point can be facilitated.

According to the present embodiment, the XY stage 12 is also capable of reciprocating displacement of the sample placement portion 121 in two directions inside the horizontal plane and includes the memory 173 storing the relative position coordinates of the position of the indenter 14a and the position where the spot of the illumination pattern is formed. The controller 17 displaces the sample placement portion 121 using the XY stage 12 based on the relative position coordinates stored in the memory 173. Therefore, the test can be performed without drifting from the adjusted test point prior to the test.

According to the present embodiment, the light source 11 is a laser light source emitting laser light. Therefore, the device can be configured with low cost.

Second Embodiment

Figure 5:
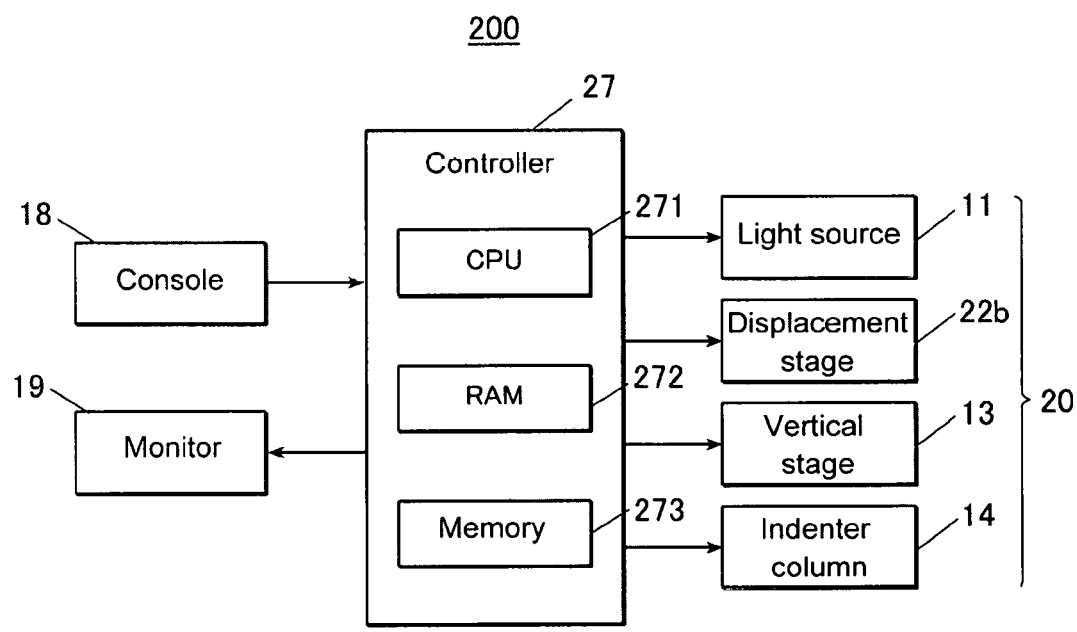
FIG. 5 is a block diagram illustrating a control structure of a hardness tester according to a second embodiment.
Figure 6:
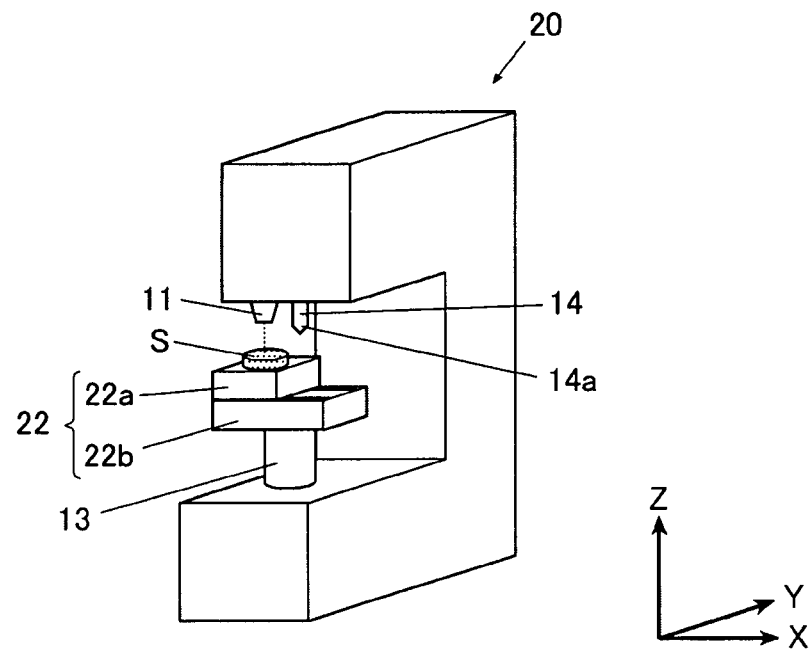
FIG. 6 is a schematic view illustrating a hardness tester main body of the hardness tester of FIG. 5.

Hereafter, a second embodiment of the present invention is described. Moreover, identical reference numerals are used for structures similar to those in the first embodiment and detailed descriptions thereof are omitted. FIG. 5 is a block diagram illustrating a control structure of the hardness tester according to the second embodiment. FIG. 6 is a schematic view illustrating a hardness tester main body of the hardness tester of FIG. 5.

As shown in FIGS. 5 and 6, a hardness tester 200 is configured to include a tester main body 20, a controller 27, the console 18, and the monitor 19.

Instead of the XY stage 12 of the first embodiment, the tester main body 20 includes a sample stage 22 configured to be displaceable in a left-right direction in a state where the sample S is placed on the sample stage 22. Further, other configurations of the tester main body 20 are identical to the tester main body 10 of the first embodiment.

The sample stage 22 includes a sample placement portion 22a on which the sample S is placed, and a displacement stage 22b which supports the sample placement portion 22a from below and slide-displaces the sample placement portion 22a in the left-right direction.

The controller 27 is configured to include a CPU 271, a RAM 272, and a memory 273. Basic configurations and functions of the CPU 271, RAM 272, and memory 273 are identical to those of the CPU 171, RAM 172, and memory 173 respectively. In the memory 273 of the present embodiment, a relative distance in the X direction is stored in advance, the relative distance lying between the position where the spot of the illumination pattern is formed by the light from the light source 11 on the top surface of the sample placement portion 22a and the position through which the perpendicular line of the vertex of the indenter 14a passes. The CPU 271 can displace the sample S in the horizontal direction to allow the perpendicular line of the vertex of the indenter 14a to be positioned at the test point on the surface of the sample S by driving the displacement stage 22b based on the relative distance.

Next, a test point alignment method of the hardness tester 200 according to the present embodiment is described. First, the user places the sample S on the top surface of the sample placement portion 22a of the sample stage 22, and performs fine adjustments to allow the spot-like illumination pattern of the light to align with the desired test point of the sample S in a state where the light is emitted from the light source 11 at the sample S. Accordingly, the position of the spot becomes the test point. In this state, when the user gives the instruction to start the test, by displacing the displacement stage 22b only by the distance stored in the memory 273, the controller 27 displaces the sample placement portion 22a and allows the desired test point of the sample S and the indenter 14a to face each other. Thereafter, the controller 27 forms the indentation at the test point on the surface of the sample S by operating the indenter 14a and calculates the hardness of the sample S using the predetermined data analysis.

As described above, according to the present embodiment, the hardness tester 200 is provided with the sample stage 22 including the sample placement portion 22a on which the sample S is placed and the displacement stage 22b which is capable of reciprocating displacement in one direction inside the horizontal plane in a state supporting the sample placement portion 22a from below. Therefore, after confirmation of the test point by emitting the light at the desired test point of the sample S, the indentation can be formed accurately at the confirmed test point.

Further, in the second embodiment mentioned above, the sample stage 22 is described to exemplify a configuration where the sample placement portion 22a is displaced by the displacement stage 22b. However, a configuration may be possible where the user manually displaces the sample placement portion 22a. Although not depicted in the drawings, such a case may be configured to support the sample placement portion 22a by a stage having stoppers at left and right predetermined locations and allow the user to slide-displace the sample placement portion 22a over the stage, for example. In this configuration, the user first places the sample S on the sample placement portion 22a with a first stopper abutting the sample placement portion 22a. In the state where light is emitted from the light source 11 at the sample S, the user performs fine adjustments to allow the illumination pattern of the light and the desired test point of the sample S to align. The user then slide-displaces the sample placement portion 22a over the stage so as to be in contact with a second stopper.

In addition, the above-described first and second embodiments are described to exemplify a configuration where the sample S (XY stage 12 or sample stage 22) displaces within the horizontal plane. However, in a case where a relative positional relationship between the sample S and the light source 11 and the indenter 14a can be changed, the sample S (XY stage 12 or sample stage 22) may be fixated and the light source 11 and the indenter 14a may be configured so as to displace within the horizontal plane.

Figure 7:
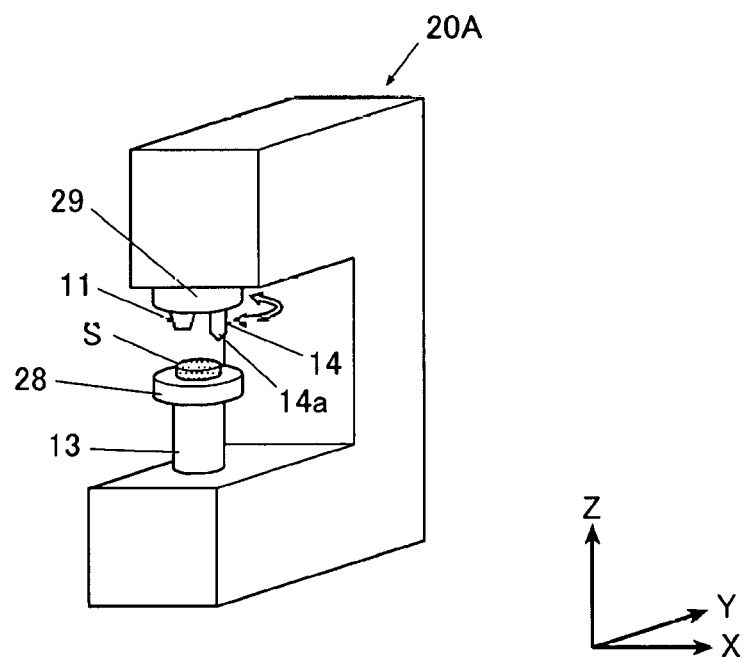
FIG. 7 is a schematic view describing a modification of the hardness testers according to the first and second embodiments.

With this configuration, as shown in FIG. 7 for example, a tester main body 20A includes a sample placement portion 28 where the sample S is placed and a turret (displacement portion or displacer) 29 displacing the indenter 14a in the horizontal direction. In addition, the turret 29 also includes the single light source 11 which is provided in parallel to the indenter 14a and emits light substantially, or generally, parallel to the vertical direction. After confirming the test point by emitting the spot-like light from the light source 11 at the surface of the sample S, the controller 27 displaces the indenter 14a in the horizontal direction by rotating the turret 29 to allow the perpendicular line of the vertex of the indenter 14a to be positioned at the test point.

Third Embodiment

Figure 8:
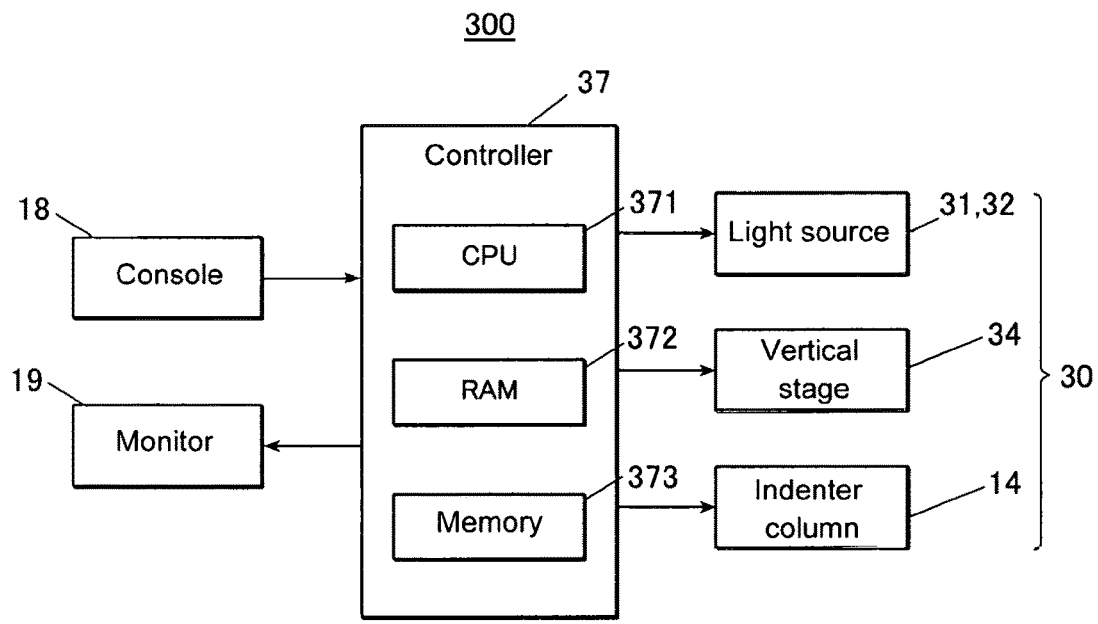
FIG. 8 is a block diagram illustrating a control structure of a hardness tester according to a third embodiment.
Figure 9:
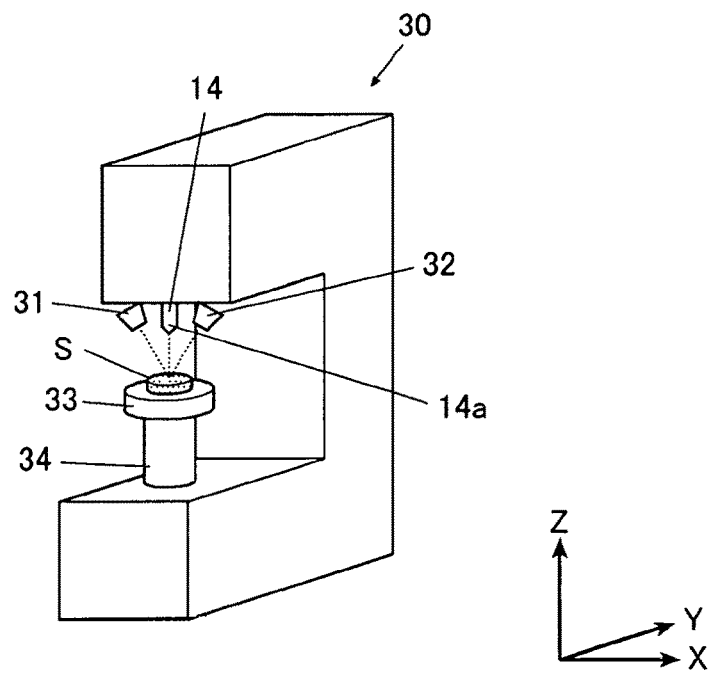
FIG. 9 is a schematic view illustrating a hardness tester main body of the hardness tester of FIG. 8.
Figure 10:
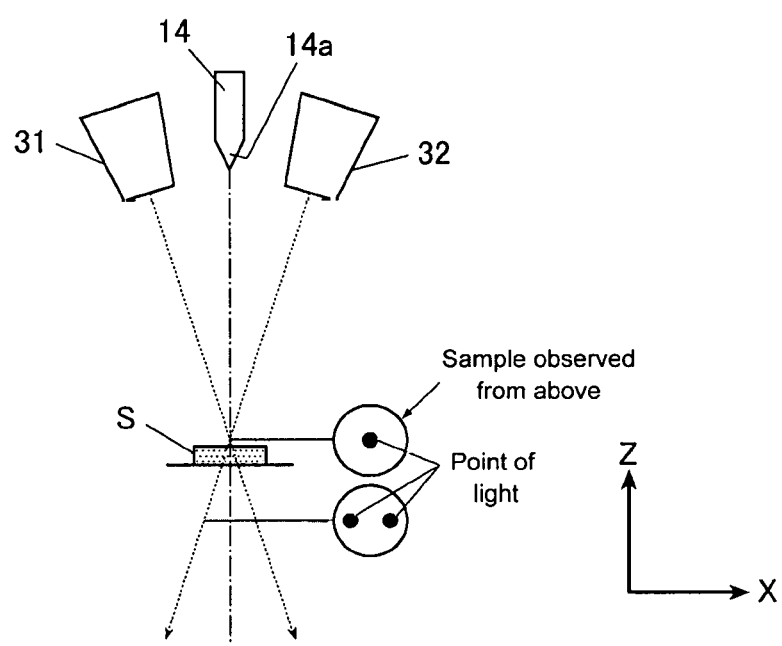
FIG. 10 illustrates a configuration of relevant portions of the tester main body of FIG. 8.

Hereafter, a third embodiment of the present invention is described. Moreover, identical reference numerals are used for structures similar to those in the first embodiment and detailed descriptions thereof are omitted. FIG. 8 is a block diagram illustrating a control structure of the hardness tester according to the second embodiment. FIG. 9 is a schematic view illustrating a hardness tester main body of the hardness tester of FIG. 8. FIG. 10 illustrates a configuration of relevant portions of the tester main body according to the present embodiment.

As shown in FIGS. 8 and 9, a hardness tester 300 is configured to include a tester main body 30, a controller 37, the console 18, and the monitor 19.

The tester main body 30, for example, is configured to include two light sources (illuminators) 31 and 32 emitting light at the sample S, a sample stage 33 where the sample S is placed, a vertical stage 34 lifting and lowering the sample stage 33, and the indenter column 14 having the indenter 14a forming the indentation on the sample S.

The two light sources 31 and 32 include LD and the like for example, and generate and emit laser light. As shown in FIG. 10, the two light sources 31 and 32 are installed with bottom ends of the light sources tilted in mutually approaching directions. The light emitted from the two light sources 31 and 32 extends in mutually approaching directions and is defined so as to intersect at the perpendicular line of the vertex of the indenter 14a (directly below the indenter 14a).

The sample stage 33 is a stage formed on the horizontal plane where the sample S can be placed on the top surface, and is supported by the vertical stage 34.

The vertical stage 34 is driven in response to the control signal output by the controller 37 and displaces the sample stage 33 in the Z direction. The vertical stage 34 adjusts a height of the sample stage 33 to allow the intersection point of the light emitted from the two light sources 31 and 32 to be positioned on the surface of the sample S. Accordingly, the spot-like illumination pattern is displayed on one point of the sample S placed on the sample stage 33.

The controller 37 is configured to include a CPU 371, a RAM 372, and a memory 373. Basic configurations and functions of the CPU 371, RAM 372, and memory 373 are similar to those of the CPU 171, RAM 172, and memory 173 respectively. The height of the sample S surface (thickness of the sample S) is stored in the memory 373 according to the present embodiment in advance prior to the test. The CPU 371, based on this height, adjusts the height of the vertical stage 34 and displays the spot-like illumination pattern on the surface of the sample S.

Next, alignment of the test point of the hardness tester 300 according to the present embodiment is described. First, the user places the sample S on the top surface of the sample stage 33. Next, with the user's instruction, the controller 37 emits light at the sample S from the two light sources 31 and 32. The controller 37 displaces the sample stage 33 in the Z direction using the vertical stage 34 and displays the spot-like illumination pattern at a single point of the sample S placed on the sample stage 33. In this state, the user performs fine adjustments to allow the illumination pattern of the light and the desired test point of the sample S to align. Thereafter, with the user's instruction, the controller 37 forms the indentation at the test point of the sample S surface by operating the indenter 14a. The controller 37 calculates the hardness of the sample S using the predetermined data analysis.

According to the present embodiment as described above, the hardness tester 300 includes the two light sources 31 and 32 emitting light in mutually approaching directions. The hardness tester 300 is configured so as to position the perpendicular line of the vertex of the indenter 14a at the spot where the light emitted from the two light sources 31 and 32 intersects. The controller 37 controls the height position of the sample S to allow the intersection point of the light emitted from the two light sources 31 and 32 to overlap the test point. Therefore, after confirming the test point by emitting the spot-like light at the desired test point of the sample S, the indentation can be formed at the confirmed test point. Therefore, with simple adjustments, the test can be performed without drifting from the adjusted test point prior to the test.

Figure 11:
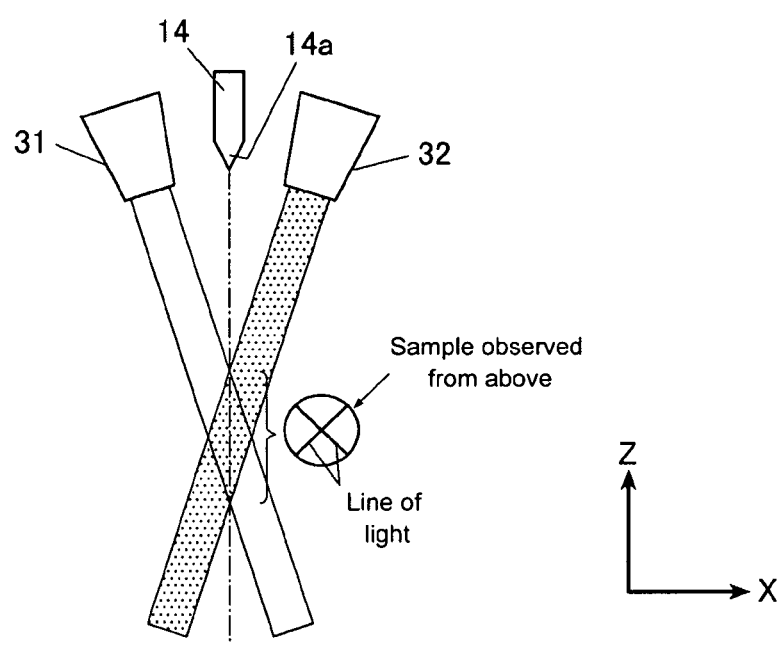
FIG. 11 illustrates a modification of the hardness tester according to the third embodiment.

The above-described third embodiment is described to exemplify a configuration of emitting line-shaped light from the two light sources 31 and 32. However, as shown in FIG. 11, a configuration is possible where a band-shaped laser light is emitted from the two light sources 31 and 32. With this configuration, the height restriction is eased and the lines of light intersect at a section with a certain width in the height direction, the intersection point (spot) can be defined as the test point.

In addition, in the first to third embodiments described above, a Rockwell hardness tester is described as exemplary. However, a Vicker's hardness tester may instead be used, for example, as a hardness tester to which the present invention can be applied.

Unless otherwise indicated, all numbers expressing quantities of ingredients and the like used in the specification and claims are to be understood as being modified in all instances by the term "about." The terms "generally" and "approximately" as used herein are to be understood as an approximation allowing for variations while still maintaining the efficacy of the invention. Accordingly, unless indicated to the contrary, the numerical and geometric parameters and relationships set forth in the present specification and attached claims are approximations that may vary depending upon the desired properties sought to be obtained by the present invention. At the very least, and not as an attempt to limit the application of the doctrine of equivalents to the scope of the claims, each numerical and geometric parameters and relationship should be construed in light of the number of significant digits and ordinary rounding approaches.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester for forming an indentation on a surface of a sample by loading a predetermined test force with an indenter, and measuring a hardness of the sample using the indentation, the hardness tester comprising:

an illuminator configured to emit light on the surface of the sample and form an illumination pattern having a spot; and a controller configured to form the indentation by bringing the indenter into contact with the sample in a state where a perpendicular line of a vertex of the indenter overlaps a test point when the position of the spot of the illumination pattern formed by the illuminator on the surface of the sample is used as the test point.

2. The hardness tester according to claim 1, further comprising:

a sample placement platform on which the sample is to be placed; and a displacer configured to displace the sample placement platform in a horizontal direction, wherein:

the illuminator includes a single light source provided in parallel to the indenter, the illuminator further configured to emit light generally parallel to a vertical direction, and the controller is further configured to displace the sample placement platform in the horizontal direction using the displacer to allow the perpendicular line of the vertex of the indenter to be positioned at the test point on the surface of the sample.

3. The hardness tester according to claim 2, further comprising:

a memory configured to store relative position coordinates of the position of the indenter and the position where the spot of the illumination pattern is formed, wherein:

the displacer includes an XY stage configured to reciprocate displacement of the sample placement platform in two directions within a horizontal plane, and the controller is configured to displace the sample placement platform using the displacer based on the relative position coordinates stored in the memory.

4. The hardness tester according to claim 1, further comprising:

a sample placement platform on which the sample is to be placed; and a displacer configured to displace the indenter in the horizontal direction, wherein the illuminator includes a single light source provided in parallel to the indenter, the illuminator further configured to emit light generally parallel to the vertical direction, and the controller is further configured to displace the indenter in the horizontal direction using the displacer to allow the perpendicular line of the vertex of the indenter to be positioned at the test point on the surface of the sample.

5. The hardness tester according to claim 1, wherein:

the illuminator includes two light sources configured to emit light in mutually approaching directions, the perpendicular line of the vertex of the indenter is configured to be positioned at the spot where the light emitted from the two light sources intersect, and the controller is further configured to control a height position of the sample to allow the intersection point of the light emitted from the two light sources and the surface of the sample to overlap.

6. The hardness tester according to claim 5, wherein the light emitted from the two light sources is band shaped.

7. The hardness tester according to claim 1, wherein the illuminator comprises a light source configured to emit laser light.

8. The hardness tester according to claim 2, wherein the illuminator comprises a light source configured to emit laser light.

9. The hardness tester according to claim 3, wherein the illuminator comprises a light source configured to emit laser light.

10. The hardness tester according to claim 4, wherein the illuminator comprises a light source configured to emit laser light.

11. The hardness tester according to claim 5, wherein the illuminator comprises a light source configured to emit laser light.

12. The hardness tester according to claim 6, wherein the illuminator comprises a light source configured to emit laser light.

* * * * *